United States Patent [19]

Eggers et al.

[11] Patent Number: 4,785,823
[45] Date of Patent: Nov. 22, 1988

[54] METHODS AND APPARATUS FOR PERFORMING IN VIVO BLOOD THERMODILUTION PROCEDURES

[75] Inventors: Philip E. Eggers, San Francisco, Calif.; Robert F. Shaw, 1750 Taylor St., Suite 2401, San Francisco, Calif. 94133

[73] Assignee: Robert F. Shaw, San Francisco, Calif.

[21] Appl. No.: 75,945

[22] Filed: Jul. 21, 1987

[51] Int. Cl.[4] ............................................. A61B 5/02
[52] U.S. Cl. ..................... 128/692; 128/713; 128/642; 128/736; 73/204.21
[58] Field of Search .................. 128/691–692, 128/736, 734, 673, 675, 713, 693–694, 642; 73/204

[56] References Cited

U.S. PATENT DOCUMENTS

| 3,269,386 | 8/1966 | Sherman | 128/713 |
| 3,304,413 | 2/1967 | Lehmann et al. | 377/19 |
| 3,347,224 | 10/1967 | Adams | 128/692 |
| 3,359,974 | 12/1967 | Khalil | 128/713 |
| 3,405,708 | 10/1968 | Webster, Jr. | 128/692 |
| 3,433,935 | 3/1969 | Sherman | 364/416 |
| 3,438,253 | 4/1969 | Kuether et al. | 73/204 |
| 3,446,073 | 5/1969 | Auphan et al. | 128/692 |
| 3,545,428 | 12/1970 | Webster, Jr. | 128/692 |
| 3,561,266 | 2/1971 | Auphan et al. | 73/204 |
| 3,604,263 | 9/1971 | Auphan et al. | 73/204 |
| 3,618,591 | 11/1971 | Bradley et al. | 128/713 |
| 3,620,207 | 11/1971 | Sinclair | 128/692 |
| 3,634,924 | 1/1972 | Blake et al. | 29/447 |
| 3,651,318 | 3/1972 | Czekajewski | 364/416 |
| 3,678,922 | 7/1972 | Philips et al. | 128/692 |
| 3,726,269 | 4/1973 | Webster, Jr. | 128/713 |
| 3,733,899 | 5/1973 | Auphan et al. | 73/204 |
| 3,798,967 | 3/1974 | Gieles et al. | 73/204 |
| 3,820,530 | 6/1974 | Gilford et al. | 128/713 |
| 3,859,602 | 1/1975 | Janssen et al. | 328/162 |
| 3,915,155 | 10/1975 | Jacobson et al. | 128/692 |
| 3,987,788 | 10/1976 | Emil | 128/713 |
| 3,995,623 | 12/1976 | Blake et al. | 128/642 |
| 4,003,370 | 1/1977 | Emil et al. | 128/673 |
| 4,004,576 | 1/1977 | Gähwiler et al. | 128/713 |
| 4,015,593 | 4/1977 | Elings et al. | 128/713 |
| 4,024,873 | 5/1977 | Antoshkiw et al. | 604/96 |
| 4,035,622 | 7/1977 | Obermajer | 128/713 |
| 4,095,117 | 6/1978 | Nagy | 250/564 |
| 4,105,022 | 8/1978 | Antoshkiw et al. | 128/713 |
| 4,120,295 | 10/1978 | Hill | 128/692 |
| 4,153,048 | 5/1979 | Magrini | 128/692 |
| 4,191,194 | 3/1980 | Watanabe et al. | 128/692 |
| 4,217,910 | 8/1980 | Khalil | 128/670 |
| 4,230,126 | 10/1980 | Elings | 128/671 |
| 4,236,527 | 12/1980 | Newbower et al. | 128/692 |
| 4,240,441 | 12/1980 | Khalil | 128/692 |
| 4,326,539 | 4/1982 | Obermajer | 128/713 |
| 4,328,806 | 5/1982 | Cooper | 604/99 |
| 4,329,993 | 5/1982 | Lieber et al. | 604/98 |
| 4,329,994 | 5/1982 | Cooper et al. | 604/98 |
| 4,361,049 | 11/1982 | Volgyesi | 73/861.05 |
| 4,380,237 | 4/1983 | Newbower | 128/734 X |
| 4,403,615 | 9/1983 | Hoehner | 128/692 |
| 4,407,298 | 10/1983 | Lentz et al. | 128/713 |
| 4,407,304 | 10/1983 | Lieber et al. | 128/786 |
| 4,417,588 | 11/1983 | Houghton et al. | 128/713 |
| 4,476,877 | 10/1984 | Barker | 128/736 |
| 4,502,488 | 3/1985 | Degironimo et al. | 128/692 |
| 4,507,974 | 4/1985 | Yelderman | 73/861.06 |
| 4,508,103 | 4/1985 | Calisi | 128/673 |
| 4,508,123 | 4/1985 | Wyatt et al. | 128/692 |
| 4,621,646 | 11/1986 | Bryant | 128/673 X |

Primary Examiner—Kyle L. Howell
Assistant Examiner—Angela D. Sykes
Attorney, Agent, or Firm—Robert R. Jackson

[57] ABSTRACT

A thermodilution catheter has electrodes in electrical contact with the blood flowing adjacent to the catheter. A potential difference applied to the electrodes causes electrical current to flow in the volume of blood in the region of the electrodes, thereby creating a bolus of blood at elevated temperature suitable for measurement of blood flow by the thermodilution principle.

39 Claims, 3 Drawing Sheets

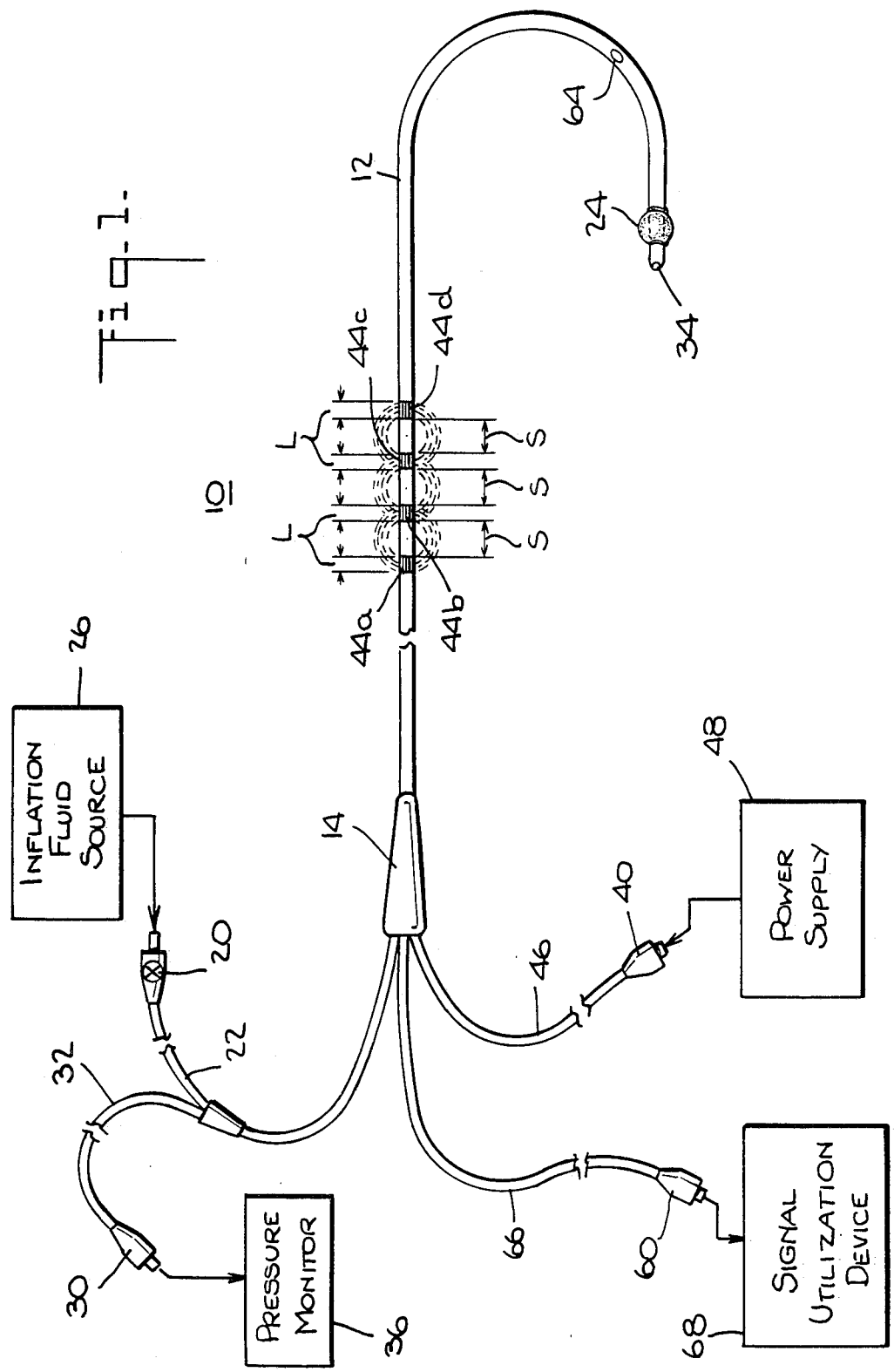

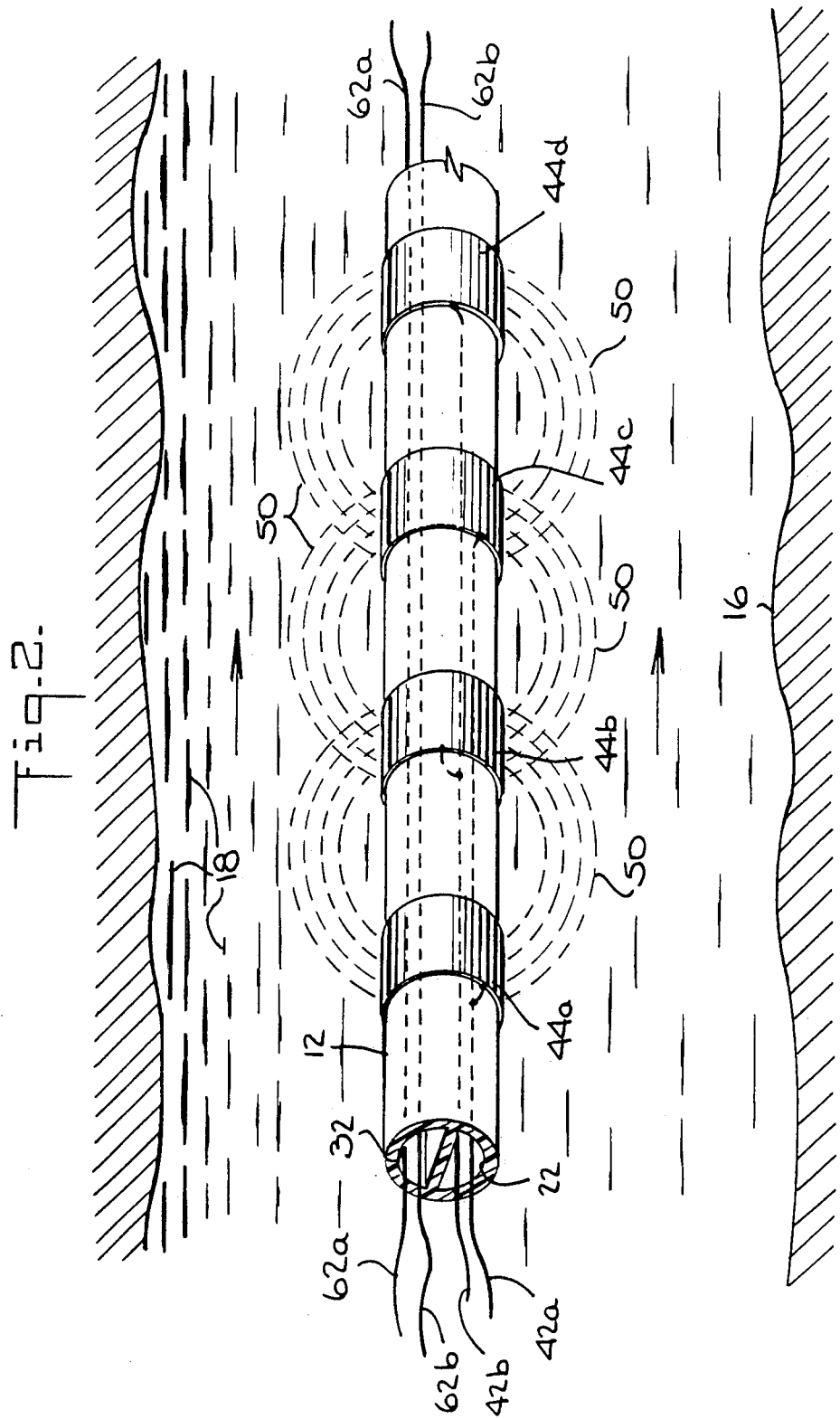

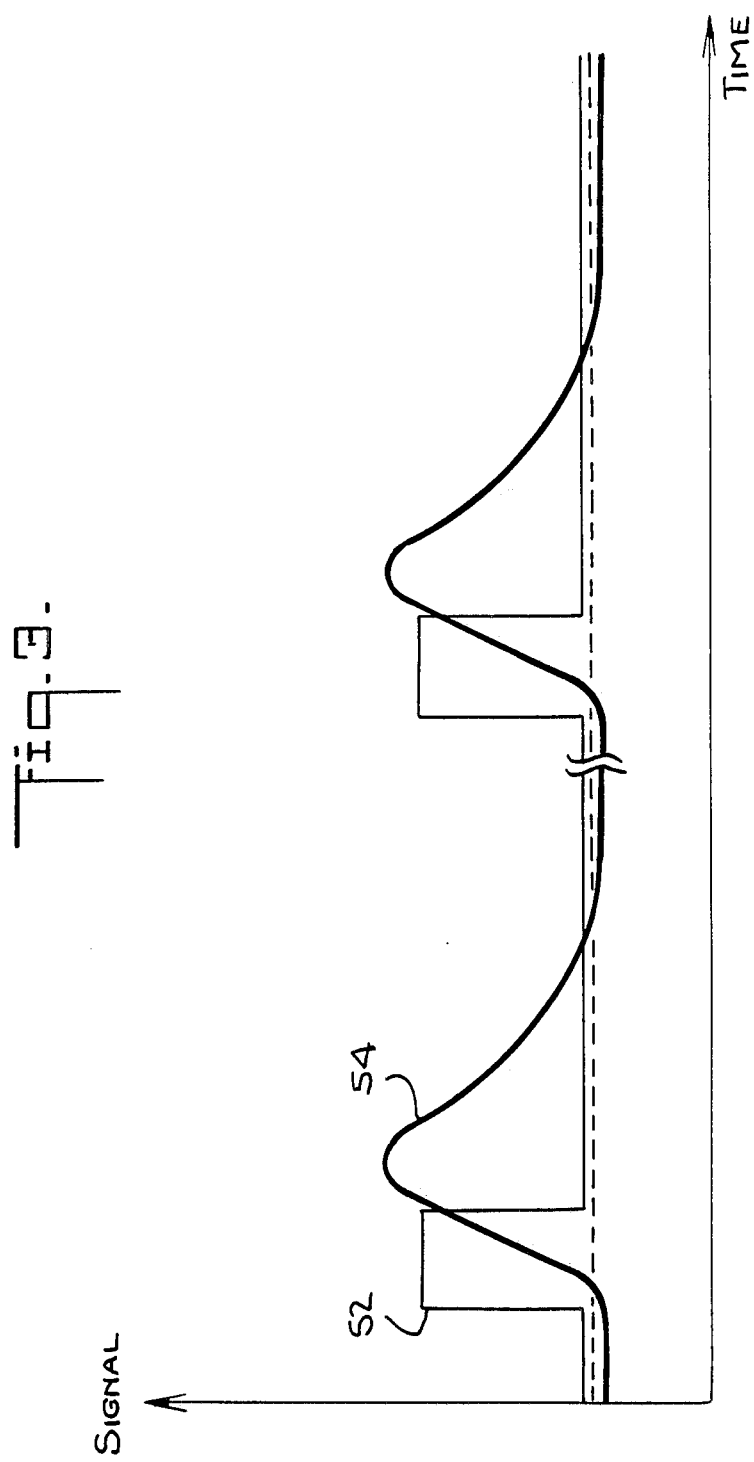

METHODS AND APPARATUS FOR PERFORMING IN VIVO BLOOD THERMODILUTION PROCEDURES

BACKGROUND OF THE INVENTION

This invention relates to methods and apparatus for performing in vivo blood thermodilution procedures, and more particularly to improved catheter methods and apparatus for use in such procedures.

One standard method for determining cardiac output is the so-called thermodilution method discussed, for example. in U.S. Pat. Nos. 3,651,318; 4,217,910; and 4,236,527. As conventionally employed, this method involves either injecting a bolus of liquid into the bloodstream at a temperature which is cooler or warmer (usually cooler) than blood temperature, or heating a segment of the blood indirectly with electrical resistance heaters, and monitoring the temperature deviation of the blood as a function of time at a location downstream from the location at which the temperature deviation is caused. The area under the resulting temperature deviation vs. time curve (known as the thermodilution curve) is a measure of the rate at which the heart is pumping blood (usually expressed in liters per minute). If cardiac output is high, the area under the thermodilution curve will be relatively small in accordance with the well-known Stewart-Hamilton relationship. Conversely, if cardiac output is low, the area under the thermodilution curve will be relatively large.

Thermodilution procedures involving the introduction of an auxialiary liquid into the blood have a number of possible deficiencies. The accuracy of these procedures depends in part on accurate knowledge of the temperature, volume, and rate of injection of the auxiliary liquid. Liquid volume measurements are difficult to make with extreme accuracy. For example, a syringe may be used, with the result that the volume may only be known to within several percent of the actual volume. Operator error associated with volume measurement and rate of injection may also be a problem. Because the catheters employed may be quite long (approximately 30 inches), it is difficult to know precisely the temperature of the liquid injectate at the point at which it enters the bloodstream near the distal end of the catheter. Heat exchange with the liquid dispensing device (e.g., the syringe), with the catheter, and with the blood and tissue surrounding the catheter upstream of the point at which the liquid is actually released into the blood may mean that the injectate temperature is also known only to within about 5% of the actual temperature. Because of the effects of the auxiliary liquid on the composition of blood stream liquid, auxiliary liquid injection techniques may not be usable repeatedly or at frequent intervals on a given patient for an extended period of time (e.g., three to six times per hour over a period of 24 to 72 hours).

Dye dilution and conductivity dilution techniques, also involving injection of an auxiliary liquid (i.e., a dye or a saline solution) into the bloodstream, are also known (see, for example, U.S. Pat. Nos. 3,269,386; 3,304,413; and 3,433,935). The resulting dye dilution or conductivity dilution curve is similar to a thermodilution curve. Dye dilution and conductivity dilution have some of the same deficiencies as auxiliary liquid thermodilution, namely, difficulty of precisely controlling the rate of injection and measuring the injectate volume, and unsuitability for frequent or repeated use over long periods of time.

The thermodilution techniques involving the use of electrical resistance heaters to heat the blood (see for example, U.S. Pat. Nos. 3,359,974; 4,217,910; and 4,240,441) may have the disadvantage of locally overheating some blood, especially if the heater or a portion of the heater happens to be close to the surrounding blood vessel so that a large amount of heat is applied to a relatively small amount of blood. This can cause undesirable coagulation of the over-heated blood. In addition, thermodilution techniques employing electrical resistance heaters transfer heat from the surface of the heater to the blood by conduction of heat into that "film" of blood in direct contact with the heated surface. Consequently, only a confined thickness of blood can be heated, limited by conduction heat transfer in blood. The amount of thermal energy that can be transferred to the blood is therefore limited since studies have shown that the blood cannot be heated to temperatures greater than 5° C. above the blood temperature without incurring blood cell damage and the formation of fibrin deposits on the surface of the heating element. Such deposits impede the transfer of heat from the surface of the heating element to the blood. The consequence of limiting the amount of heat which can be delivered to the blood by prior art methods is that the amount of thermal energy imparted to the blood, i.e., the "indicator", is too small to allow for the accurate measurement of cardiac output by conventional thermodilution techniques.

In view of the foregoing, it is an object of this invention to improve the methods and apparatus employed in thermodilution procedures.

It is more particular object of this invention to provide methods and apparatus for improving the reliability, accuracy, and repeatability of thermodilution procedures.

It is still another object of the invention to provide thermodilution methods and apparatus that can be used on a given patient with increased frequency over time periods of increased length.

SUMMARY OF THE INVENTION

These and other objects of the invention are accomplished in accordance with the principles of the invention by providing methods and apparatus for directly heating the blood by passing an electrical current through it between two (or more) spaced electrodes, each of which is in electrical contact with the blood. Typically the electrodes are mounted on a catheter or other similar longitudinal support member which is inserted longitudinally in the blood vessel in which blood flow is to be measured. Preferably, each electrode extends annularly around the support member, and the electrodes are longitudinally spaced from one another. An electrical potential difference is applied to the electrodes, preferably via wires in the support member. These wires may be coaxial, twisted, or twisted with surrounding electromagnetic shielding to minimize stimulation of tissue adjacent to the wires and/or interaction with other patient monitoring devices (e.g., electrocardiographs). The electrical potential difference applied to the electrodes is preferably a alternating current ("AC") potential difference having a frequency selected to minimize any muscle stimulation in the heart or surrounding tissue. This is typically a frequency of at least about 20 KHz. Although the magnitude and duration of the current may be varied, typical magnitudes are approximately 1 ampere at 100 volts, and typical durations are about 2 to 4 seconds. A temperature sensor is located in the bloodstream downstream from the electrodes, typically by being mounted on the support member. The temperature sensor produces an output (e.g., an electrical signal) indicative of the temperature of the blood adjacent to the sensor. This output, which is a conventional thermodilution curve, can be processed by any conventional thermodilution curve processing technique to provide an accurate measurement of the rate of blood flow (e.g., liters per minute) in the blood vessel. If the apparatus is positioned in a vessel carrying substantially all of the blood flowing through the heart, then the measurement referred to above is a measurement of cardiac output.

The heating method utilized in this invention offers significant advantages over the prior art since thermal energy is imparted directly in a volume of blood defined by the size and relative spacing of the electrodes and does not depend on conducting heat into the blood from a heated surface. The benefit of this distributed heating method is that the thermal energy level required for an accurate cardiac output measurement can be imparted to a volume of blood several orders of magnitude larger than can be heated, during the same time interval, using a heated surface as the source of thermal energy. As a consequence of using the heating method of the present invention, the temperature rise of the blood which results from imparting a given quantity of thermal energy is significantly lower than the corresponding temperature rise using the surface heating methods. In this manner, the requisite quantities of thermal energy required for measuring cardiac output using the thermodilution method can be safely imparted while minimizing the risk of damage to the blood or thrombus formation.

In addition, the technique of the present invention minimizes the danger to any tissues (e.g., blood vessels and tissues lining the interior of the heart) since the electrodes of the present method are not heated but, rather, heat the volume of electrically conducting medium which surrounds and is disposed between the electrodes. Because such tissues generally have higher electrical resistance than blood, the electrical currents will flow preferentially in the blood, thereby minimizing any heating within any adjacent tissue. A further benefit of the heating technique of the present invention is that the distributed heating of the blood allows the unheated electrodes to be maintained close to the temperature of the surrounding blood. As a consequence, the thermal mechanisms which otherwise lead to and/or accelerate the formation of coatings (e.g., fibrin formation) on the surface of the electrodes will be minimized.

As mentioned above, the support member may be a catheter. The catheter may have other conventional features such as a distal balloon or inflatable annular ring for facilitating passage of the catheter through portions of the heart (e.g., through the right atrium and right ventricle into the pulmonary artery). The catheter may also have a conventional distal pressure sensing capability for monitoring the blood pressure at the distal end of the catheter and thereby providing information helpful in determining how far the catheter should be inserted (e.g., by confirming that the distal end of the catheter has passed through the right atrium, right ventricle, and pulmonary artery, and that it has reached the pulmonary wedge and is to some extent withdrawn.)

Further features of the invention, its nature and various advantages will be more apparent from the accompanying drawings and the following detailed description of the invention.

BRIEF DESCRIPTION OF THE DRAWINGS

FIG. 1 is a partial view of the catheter of this invention. Apparatus that may be used in conjunction with the catheter is shown in block diagram form.

FIG. 2 is an enlargement of a portion of the catheter of FIG. 1 in use in a blood vessel.

FIG. 3 is a signal diagram useful in explaining the principles and operation of the invention.

DETAILED DESCRIPTION OF THE INVENTION

Although the electrodes of this invention can be introduced by other means into the blood vessel with respect to which the thermodilution procedure is to be carried out, it is particularly advantageous in many applications of the invention to mount the electrodes on an otherwise largely conventional catheter. Accordingly, the invention will be described for the most part in relation to a catheter embodiment, and particularly in relation to a catheter embodiment useful in determining cardiac output by measuring blood flow in the pulmonary artery. It will be understood, however, that the invention is equally applicable to measuring blood flow in any vessel into which the electrodes of the invention can be inserted, and that the electrodes (and other elements such as the downstream blood temperature sensor) need not be mounted on a catheter. For example, the electrodes (and temperature sensor) could be mounted on any support member that is insertable in the blood vessel.

In the particular illustrative embodiment shown in FIG. 1, catheter 10 includes an elongated distal portion 12 that is insertable in a blood vessel in the manner shown, for example, in U.S. Pat. Nos. 3,995,623; 4,217,910; 4,230,126; 4,236,527; and 4,240,441. The proximal portion 14 of catheter 10 remains outside the patient's body at all times.

Catheter 10 is of generally conventional multilumen construction (see, for example, U.S. Pat. Nos. 3,359,974; 3,634,924; 3,995,623; 4,328,806; 4,329,993; 4,329,994; and 4,407,304). One of its lumens 22 extends from proximal connector 20 to the interior of distal inflatable annular ring or balloon 24 (see also FIG. 2). A suitable fluid such as carbon dioxide may be forced into lumen 22 via connector 20 from a conventional inflation fluid source 26 such as a syringe to inflate balloon 24 as shown in FIG. 1. In the absence of such fluid pressure from lumen 22, balloon 24 tends to collapse so that it is of approximately the same diameter as the insertable portion 12 of catheter 10. U.S. Pat. Nos. 3,634,924; 3,995,623; 4,236,527; 4,328,806; 4,329,993; 4,329,994; and 4,407,304, among other references, show that such balloon catheter construction is conventional. Inflation fluid source 26 may be removably connectable to connector 20.

Another lumen 32 of catheter 10 extends from proximal connector 30 to an opening 34 at the distal end of the catheter. In use, this lumen is filled with (or fills with) liquid such as electrolyte solution or blood so that blood pressure at opening 34 can be monitored by pressure monitor 36, which is typically removably connectable to connector 30. Monitoring pressure in this way is well known to those skilled in the art (see, for example, U.S. Pat. Nos. 3,995,623; 4,328,806; 4,329,993; 4,329,994; and 4,407,304), and pressure monitor 36 may be entirely conventional.

Near the distal end of the insertable portion 12 of catheter 10 (but proximal of balloon 24) are at least two electrodes 44a, 44b, 44c, etc. Each of electrodes 44 is mounted on catheter 10 so that when the catheter is inserted in a blood vessel, each electrode is in electrical contact with the blood in that vessel. Although other sizes, shapes, and spacings may employed for electrodes 44, the preferred electrodes are annular rings around the outside of catheter 10, each electrode being approximately 0.1 to 0.5 inches long parallel to the longitudinal axis of the catheter (the dimension L in FIG. 1), and spaced from the adjacent electrode (or electrodes) by approximately 0.5 to 2.0 inches (the dimension S in FIG. 1). The preferred electrode length and spacing depends on the number of electrodes included with the objective of maintaining localized heating of the blood within acceptable levels. Electrodes 44 are preferably made of a material which is nontoxic, biologically inert, and a good conductor of electricity. Suitable materials include platinum and surgically acceptable grades of stainless steel. Each electrode 44 may be formed by winding a wire around catheter 10, by wrapping a foil strip around the catheter, by placing a metal ring around the catheter, or by any other suitable technique that secures the electrode to the catheter and leaves the electrode exposed for electrical contact with the blood that surrounds the catheter in use.

Insulated wires 42a and 42b are disposed in catheter 10 as best seen in FIG. 2. Wires 42a and 42b may be coaxial, twisted pair, or twisted pair with an external electromagnetic shield member to minimize the radiation of electromagnetic energy to the surrounding tissue and/or patient monitoring devices (e.g., electrocardiographs). In the depicted embodiment, wires 42 pass through lumen 22 in the insertable portion 12 of catheter 10. In the noninsertable portion 14, however, wires 42 diverge from lumen 22 and pass inside protective sheath 46 to coupler 40. Coupler 40 is removably connectable to power supply 48 for supplying power to electrodes 44 via wires 42.

Wires 42a and 42b are respectively connected to alternate ones of electrodes 44 so that the electrical potential difference applied to wires 42a and 42b by power supply 48 is conveyed to adjacent pairs of electrodes 44. In particular, wire 42a is connected to electrodes 44a and 44c, while wire 42b is connected to electrodes 44b and 44d. Accordingly, the potential difference applied to wires 42a and 42b causes the same potential difference to exist between electrodes 44a and 44b, between electrodes 44b and 44c, and between electrodes 44c and 44d. When catheter 10 is inserted in blood vessel 16 as shown in FIG. 2, these potential differences cause electrical current to flow through the blood 18 in the vessel between adjacent pairs of electrodes as indicated by electrical current flow lines 50 in FIG. 2. The temperature of the blood through which current 50 flows increases as a result of the current flow.

Downstream from electrodes 44 (but preferably upstream from balloon 24) is temperature sensor 64. Temperature sensor 64 may be any conventional device in good thermal contact with the blood flowing past the catheter for producing an output indication of the temperature of the blood at the location of sensor 64. In the depicted embodiment, temperature sensor 64 is a thermistor connected to signal utilization device 68 by insulated wires 62a and 62b. Inside the distal portion 12 of catheter 10 wires 62 pass along lumen 32. In the proximal portion of the catheter, however, wires 62 diverge from lumen 32 and pass through protective sheath 66 to coupler 60. Coupler 60 is typically removably connectable to device 68. In use, when the blood is heated by electrical current from electrodes 44 as described above, the output signal of sensor 64 will represent or indicate the resulting thermodilution curve. This thermodilution curve is entirely conventional. Accordingly, device 68 may be any conventional apparatus for processing signals representative of such curves (see, for example, U.S. Pat. Nos. 3,269,386; 3,304,413; 3,618,591; 3,651,318; 3,678,922; 3,859,602; 3,915,155; 3,987,788; 4,015,593; 4,120,295; and 4,361,049). In the simplest case, device 48 may be a conventional plotter for plotting the thermodilution curve output signal of sensor 64 as a function of time. The area under the plotted thermodilution curve can be measured by hand using a conventional planimeter or by conventional numerical integration techniques.

Power supply 48 is preferably an alternating current ("AC") power supply. The frequency of the power supplied by power supply 48 is preferably chosen to minimize any muscle stimulation in the heart or surrounding tissue. This is typically a frequency of at least about 20 KHz, and preferably a frequency in the range from about 200 KHz to about 500 KHz.

Power supply 48 is preferably operated to produce a short burst of power (represented by line 52 in FIG. 3) whenever it is desired to take a thermodilution measurement. Typically the duration of such a pulse is in the range from about 2 to about 4 seconds. This is optimum for power delivery and accurate thermodilution measurement. The resulting output signal of temperature sensor 64 (which, as mentioned above, is the thermodilution curve) is represented by line 54 in FIG. 3. Although the voltage and amperage of the current may depend on the application and construction of the apparatus, typical voltages are in the range from about 60 to about 120 volts RMS, and typical amperages are in the range from about 0.5 to 1.5 amps RMS. In general, for example, the more electrodes 44 the catheter has, the lower the applied voltage can be.

Advantageously, with the apparatus of this invention the voltage, amperage, and pulse duration can be very precisely predetermined and/or measured so that the amount of energy delivered to the blood via electrodes 44 and the duration of that energy injection are very accurately known. This greatly increases the accuracy of thermodilution measurements taken in accordance with this invention as compared to such prior art methods as the cold bolus method in which the input parameters (such as injectate volume and temperature) are not known with comparable accuracy. In accordance with the present invention, blood flow (e.g., cardiac output) in liters per minute is determined from the following relationship:

$$\text{Blood Flow, liters/minute} = \frac{C \times Q \times 60}{R \times H \times A \times 1000}$$

where
C = correction factor to account for thermal losses
Q = total energy injected into blood, calories
60 = conversion factor from seconds to minutes 1000 = conversion factor from cubic centimeters to liters
R = density of blood, gram/cubic centimeter
H = specific heat of blood, calories/gram/°C.
A = area under thermodilution curve, °C.-sec.

Because the variable Q in this relationship is a product of applied volts, amps, and time, all of which can be known with great precision, the resulting blood flow determination can be made with corresponding precision.

Unlike liquid injection thermodilution or dye dilution procedures, the procedure of this invention can be repeated fairly frequently (e.g., at intervals as short as about 5 minutes) over relatively long periods of time (e.g., 24 to 72 hours or more). As compared to thermodilution methods employing the indirect heating of blood using surface heating electrical resistance heaters, there is less likelihood of local overheating of a portion of the blood because the present invention utilizes dispersed or distributed heating of a volume of blood rather than localized heating of the blood through transfer from a heated surface.

In a particularly preferred use of the invention, cardiac output is measured by employing catheter 10 in the manner generally shown in U.S. Pat. Nos. 3,995,623; 4,015,593; 4,236,527; 4,328,806; 4,329,993; 4,329,994; and 4,407,304. The insertable portion 12 of catheter 10 is fed into a vein, thence through the right atrium, right ventricle, and into the pulmonary artery. The progress of the distal end of the catheter is monitored by means of pressure monitor 36. Passage of the distal end of the catheter through the heart is facilitated by operating inflation fluid source 26 to inflate balloon 24. Insertion of the catheter is stopped when pressure monitor 36 detects the pulmonary wedge pressure. This means that the distal end of the catheter has reached the pulmonary wedge position. Electrodes 44 will then be located in or near the right atrium and temperature sensor 64 will be located in the pulmonary artery. Power supply 48 and signal utilization device 68 can then be operated as described above to measure blood flow (in liters per minute) in the pulmonary artery in order to determine cardiac output.

Good cardiac output measurement accuracy has been achieved under the following conditions using this invention: First, the catheter included two electrodes with each electrode (platinum or platinum-plated metal) 7 millimeters in length and separated by a distance (between the interior edges of the electrodes) of 30 millimeters. The proximal electrode (i.e., the electrode closest to the external connections) was located 30 centimeters from catheter tip 34 for adult use, or 20 centimeters from tip 34 for "small anatomy" situations, or 15 centimeters from tip 34 for pediatric use. The energy pulse was accomplished with an applied voltage of about 100 volts (RMS) and 1.0 amps (RMS) at a frequency of 200 to 500 KHz and for a duration of 2.5 seconds.

The U.S. patents referred to above are all incorporated by reference herein. However, it is not believed that any of those patents contain material that is essential for understanding or practicing this invention.

Although particular embodiments of the invention have been shown and described, it will be understood that various modifications can be made by those skilled in the art without departing from the scope and spirit of the invention. For example, although four electrodes 44 are employed in the depicted embodiment, as few as two, or more than four such electrodes could be employed. Similarly, although use of the catheter to measure cardiac output in the pulmonary artery has been described, the catheter is equally useful for measuring blood flow in other areas of the body.

We claim:

1. Apparatus for use in in vivo blood thermodilution procedures comprising:
   a first electrode insertable in a blood vessel so that the first electrode is in electrical contact with the blood flowing in the blood vessel;
   a second electrode insertable in the blood vessel so that the second electrode is spaced from the first electrode and in electrical contact with the blood flowing in the blood vessel;
   first means for conveying a first electrical potential to the first electrode;
   second means for conveying a second electrical potential to the second electrode so that when the first and second electrical potentials are different from one another, electrical current flows between the first second electrodes through the blood flowing in the blood vessel to heat the blood through which said current flows; and
   a temperature sensor insertable in the blood vessel at a temperature sensing location downstream from the first and second electrodes for producing an output indication of the temperature of the blood at the temperature sensing location.

2. The apparatus defined in claim 1 further comprising:
   means disposed outside the body of the thermodilution procedure patient for applying an electrical potential difference to the first and second means for conveying.

3. The apparatus defined in claim 2 wherein the means for applying applies an alternating current potential difference having a frequency of at least about 20 KHz for a period of approximately 2 to 4 seconds.

4. The apparatus defined in claim 2 wherein the means for applying applies an alternating current potential difference having a frequency in the range from about 200 KHz to about 500 KHz.

5. The apparatus defined in claim 1 further comprising:
   means disposed outside the body of the thermodilution procedure patient for monitoring the output of the temperature sensor as a function of time.

6. The method of performing an in vivo blood thermodilution procedure by heating a portion of the blood flowing in a blood vessel and monitoring the temperature of the blood at another point in the blood stream comprising the steps of:
   inserting a first electrode in the blood vessel so that the first electrode is in electrical contact with the blood flowing in the blood vessel;
   inserting a second electrode in the blood vessel so that the second electrode is spaced form the first electrode and in electrical contact with the blood flowing in the blood vessel;
   applying an electrical potential difference to the first and second electrodes so that an electrical current flows through the blood between the first and second electrodes and heats the blood through which the current flows; and
   inserting a temperature sensor in the blood vessel at a temperature sensing location downstream from the first and second electrodes for producing an output indication of the temperature of the blood at the temperature sensing location.

7. The method defined in claim 6 wherein the electrical potential difference is an alternating current potential difference having a frequency of at least about 20 KHz.

8. The method defined in claim 6 wherein the electrical potential difference is applied for a period of approximately 2 to 4 seconds.

9. The method defined in claim 6 wherein the electrical potential difference is an alternating current potential difference having a frequency in the range from about 200 KHz to about 500 KHz.

10. The method defined in claim 6 further comprising the step of:
monitoring the output of the temperature sensor as a function of time.

11. Apparatus for use in in vivo blood thermodilution procedures comprising:
a longitudinal support member, at least a portion of which is longitudinally insertable into a longitudinal blood vessel so that the longitudinal axis of the inserted portion of the support member and the longitudinal axis of the blood vessel are substantially aligned;
a first electrode disposed on the inserted portion of the support member so that it is in electrical contact with the blood flowing in the blood vessel;
a second electrode disposed on the inserted portion of the support member so that it is spaced from the first electrode and in electrical contact with the blood flowing in the blood vessel;
means for conveying an electrical potential difference to the first and second electrodes for causing an electrical current to flow through the blood between the first and second electrodes and thereby heat the blood through which the current flows; and
a temperature sensor disposed on the inserted portion of the support member at a temperature sensing location downstream from the first and second electrodes for producing an output indication of the temperature of the blood at the temperature sensing location.

12. The apparatus defined in claim 11 further comprising:
means disposed outside the body of the thermodilution procedure patient for applying the electrical potential difference to the means for conveying.

13. The apparatus defined in claim 12 wherein the means for applying applies an alternating current potential difference having a frequency of at least about 20 KHz for a period of approximately 2 to 4 seconds.

14. The apparatus defined in claim 12 wherein the means for applying applies an alternating current potential difference having a frequency in the range from about 200 KHz to about 500 KHz.

15. The apparatus defined in claim 11 further comprising:
means disposed outside the body of the thermodilution procedure patient for monitoring the output of the temperature sensor as a function of time.

16. The method of performing an in vivo thermodilution procedure on the blood flowing in a blood vessel comprising the steps of:
providing a longitudinal support member having spaced first and second electrodes;
inserting the support member longitudinally in a longitudinal blood vessel so that the longitudinal axes of the support member and the blood vessel are substantially aligned and so that each of the first and second electrodes is in electrical contact with the blood flowing in the blood vessel;
applying an electrical potential difference to the first and second electrodes so that electrical current flows through the blood between the first and second electrodes and heats the blood through which the current flows; and
inserting a temperature sensor in the blood vessel at a temperature sensing location downstream from the first and second electrodes for producing an output indication of the temperature of the blood at the temperature sensing location.

17. The method defined in claim 16 wherein the electrical potential difference is in alternating current potential difference having a frequency of at least about 20 KHz.

18. The method defined in claim 16 wherein the electrical potential difference is applied for a period of approximately 2 to 4 seconds.

19. The method defined in claim 16 wherein the electrical potential difference is an alternating current potential difference having a frequency in the range from about 200 KHz to about 500 KHz.

20. The method defined in claim 16 further comprising the step of:
monitoring the output of the temperature sensor as a function of time.

21. A catheter for use in in vivo blood thermodilution procedures comprising:
a longitudinal member insertable longitudinally into a blood vessel;
a first electrode disposed on the longitudinal member so that the first electrode is in electrical contact with the blood flowing in the blood vessel;
a second electrode disposed on the longitudinal member so that the second electrode is spaced from the first electrode and in electrical contact with the blood flowing in the blood vessel;
means for conveying an electrical potential difference longitudinally along the longitudinal member to the first and second electrodes for causing an electrical current to flow through the blood between the first and second electrodes and thereby heat the blood through which the current flows; and
means disposed on the longitudinal member for sensing the temperature of the blood flowing in the blood vessel at a temperature sensing point downstream from the first and second electrodes.

22. The catheter defined in claim 21 wherein the means for conveying is selected from the group consisting of coaxial cable, twisted pair wire, and twisted pair wire surrounded by an electromagnetic shield.

23. The catheter defined in claim 21 wherein the means for sensing the temperature of the blood comprises a thermistor disposed on the longitudinal member at the temperature sensing point.

24. The catheter defined in claim 23 wherein each of the first and second electrodes is an annular member extending annularly around the longitudinal axis of the longitudinal member.

25. The catheter defined in claim 24 wherein the longitudinal spacing between the first and second electrodes is in the range from about 0.5 to about 2.0 inches, and the width of each electrode, measured parallel to the longitudinal member, is in the range from about 0.1 to about 0.5 inches.

26. The catheter defined in claim 21 wherein the means for conveying an electrical potential difference comprises first and second electrical conductors respectively connected to the first and second electrodes and disposed in the longitudinal member.

27. The catheter defined in claim 21 wherein the means for sensing the temperature of the blood comprises a thermistor disposed on the longitudinal member at the temperature sensing point.

28. The catheter defined in claim 27 wherein the means for sensing the temperature of the blood further comprises first and second electrical leads disposed in the longitudinal member and connected to the thermistor.

29. The catheter defined in claim 21 further comprising:
   means associated with the longitudinal member for sensing the pressure of the blood flowing in the blood vessel at a pressure sensing point downstream from the first and second electrodes.

30. The catheter defined in claim 29 wherein the means for sensing the pressure of the blood comprises a first longitudinal conduit extending longitudinally through the longitudinal member to the pressure sensing point.

31. The catheter defined in claim 21 further comprising:
   an inflatable annular ring disposed on the longitudinal member at a location downstream from the first and second electrodes; and
   means associated with the longitudinal member for selectively inflating the annular ring.

32. The catheter defined in claim 31 wherein the means for selectively inflating comprises a second longitudinal conduit extending longitudinally through the longitudinal member to the annular ring.

33. The method of determining cardiac output comprising the steps of:
   inserting into a blood vessel carrying substantially all the blood flowing through the heart a catheter having a plurality of electrodes in electrical contact with the blood and a temperature sensor in thermal contact with the blood at a temperature sensing location downstream from the electrodes for producing an output indicative of the temperature of the blood at the temperature sensing location;
   applying an electrical potential difference to the electrodes for a predetermined time interval so that electrical current flows between the electrodes through the blood and heats the blood through which the current flows; and
   monitoring the temperature sensor output as a function of time.

34. The method defined in claim 33 wherein the electrical potential difference is applied to the electrodes for a time interval of approximately 2 to 4 seconds.

35. The method defined in claim 33 wherein the electrical potential difference is an alternating current potential difference having a frequency of at least about 20 KHz.

36. The method defined in claim 33 wherein the electrical potential difference is an alternating current potential difference having a frequency in the range from about 200 KHz to about 500 KHz.

37. The method defined in claim 33 wherein the catheter is inserted via a vein through the right atrium and right ventricle of the heart and into the pulmonary artery so that the electrodes are disposed in or near the right atrium and the temperature sensor is disposed in the pulmonary artery when the electrical potential difference is applied to the electrodes.

38. The method defined in claim 37 wherein the catheter includes an inflatable annular ring downstream from the electrodes and the temperature sensor, and wherein the method further comprises the step of inflating the annular ring during passage of that portion of the catheter through the right atrium and right ventricle.

39. The method defined in claim 38 wherein the catheter includes a blood pressure sensing point downstream from the annular ring, and wherein the method further comprises the step of monitoring the blood pressure at the blood pressure sensing point during insertion of the catheter and inserting the catheter until the pulmonary capillary wedge pressure is detected at the blood pressure sensing point.

* * * * *

UNITED STATES PATENT AND TRADEMARK OFFICE
CERTIFICATE OF CORRECTION

PATENT NO. : 4,785,823
DATED : November 22, 1988
INVENTOR(S) : Philip E. Eggers and Robert F. Shaw It is certified that error appears in the above-identified patent and that said Letters Patent is hereby corrected as shown below:

Change claim 23 to read:

--23. The catheter defined in claim 21 wherein the first and second electrodes are spaced from one another longitudinally along the longitudinal member.--

Signed and Sealed this

Twenty-fifth Day of June, 1991

Attest:

HARRY F. MANBECK, JR.

*Attesting Officer*

Commissioner of Patents and Trademarks